US00PP18856P2

(12) United States Plant Patent
Trees

(10) Patent No.: US PP18,856 P2
(45) Date of Patent: May 27, 2008

(54) ***VERBENA* PLANT NAMED 'BALAZLIPI'**

(50) Latin Name: *Verbena×hybrida*
Varietal Denomination: Balazlipi

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 67 days.

(21) Appl. No.: 11/602,870

(22) Filed: Nov. 20, 2006

(51) Int. Cl.
*A01H 5/00* (2006.01)

(52) U.S. Cl. ..... Plt./308
(58) Field of Classification Search ..... Plt./308
See application file for complete search history.

*Primary Examiner*—Annette H Para
(74) *Attorney, Agent, or Firm*—Audrey Charles

(57) ABSTRACT

A new and distinct cultivar of *Verbena* plant named 'Balazlipi', characterized by its very light pink-colored flowers, medium green-colored foliage, and moderately vigorous and trailing, spreading growth habit.

1 Drawing Sheet

Latin name of genus and species of plant claimed: *Verbena×hybrida.*
Variety denomination: 'Balazlipi'.

BACKGROUND OF THE INVENTION

The present invention relates to a new and distinct cultivar of *Verbena* plant botanically known as *Verbena×hybrida* and hereinafter referred to by the cultivar name 'Balazlipi'.

The new cultivar originated in a controlled breeding program in Arroyo Grande, Calif. during January 2004. The objective of the breeding program was the development of *Verbena* cultivars with unique flower coloration and a vigorous trailing, spreading growth habit.

The new *Verbena* cultivar is the result of cross-pollination. The female (seed) parent of the new cultivar is Aztec® Dark Purple Improved 'Balazdapi'. U.S. Plant Pat. No. 12,807, characterized by its dark lavender-colored flowers, medium green-colored foliage, and mounded-trailing growth habit. The male (pollen) parent of the new cultivar is the proprietary *Verbena×hybrida* breeding selection designated 1671-1, not patented, characterized by its pure white-colored flowers, dark green-colored foliage, and semi-trailing, well-branched growth habit. The new cultivar was discovered and selected as a single flowering plant within the progeny of the above stated cross-pollination during July 2004 in a controlled environment at Arroyo Grande, Calif.

Asexual reproduction of the new cultivar by terminal stem cuttings since July 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balazlipi' as a new and distinct cultivar of *Verbena* plant:

1. Very light pink-colored flowers;
2. Medium green-colored foliage; and

3. Moderately vigorous and trailing, spreading growth habit.

Plants of the new cultivar differ from plants of the female parent primarily in flower color and growth habit and from plants of the male parent primarily in flower color, flower size, and foliage color.

Of the many commercially available *Verbena* cultivars known to the inventor, the most similar in comparison to the new cultivar is Aztec® Lilac Picotee 'Balazpico', U.S. Plant Pat. No. 14,652. However, in side by side comparisons, plants of the new cultivar differ from plants of 'Balazpico' in the following characteristics:

1. Plants of the new cultivar have larger flowers than plants of 'Balazpico';
2. Plants of the new cultivar have more compact inflorescences than plants of 'Balazpico' and
3. Plants of the new cultivar have a flower color different from plants of 'Balazpico'.

In addition, plants of the new cultivar are similar in comparison to 'Balazpink', U.S. Plant Pat. No. 14,529. However, based on information in the plant patent, plants of the new cultivar have a flower color different from plants of 'Balazpink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazlipi'. The plants were grown in 4.5 inch pots for 13 weeks in a greenhouse at West Chicago, Ill.

DETAILED BOTANICAL DESCRIPTION

Figure 1:
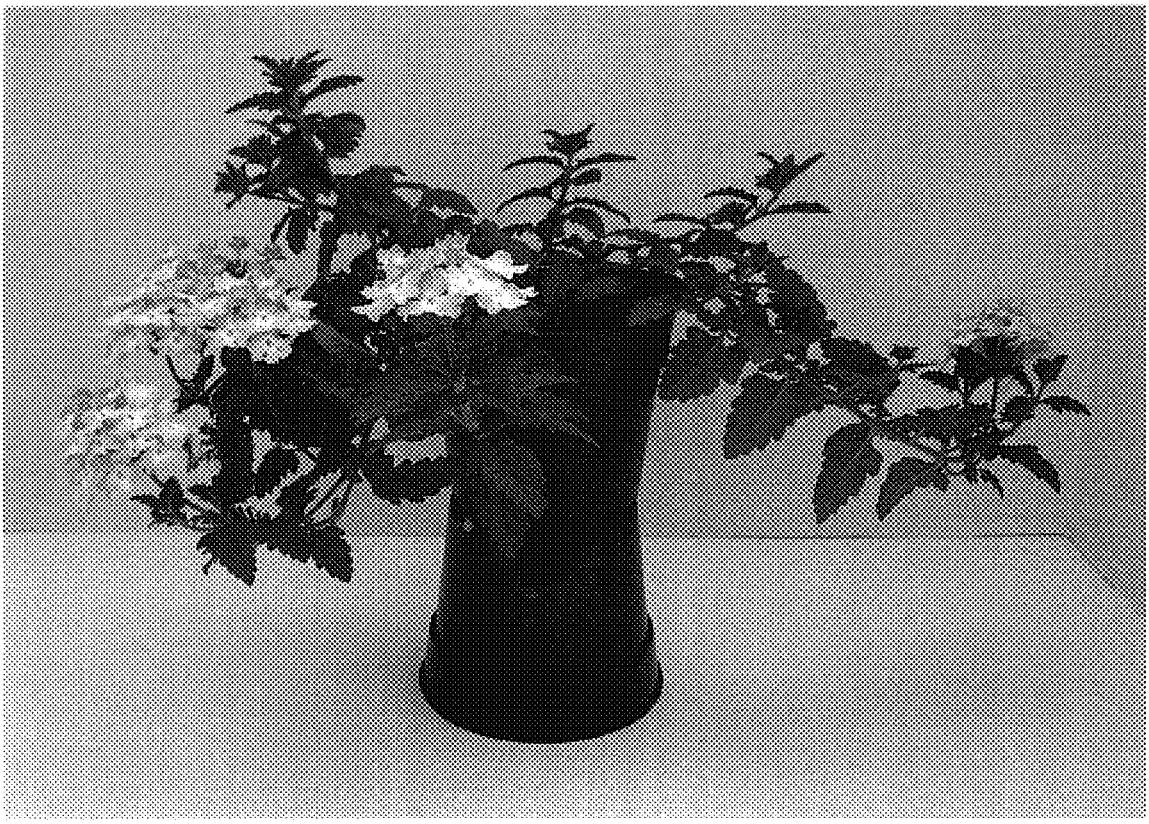
FIG. 1 illustrates a side view of the overall growth and flowering habit of 'Balazlipi'.
Figure 2:
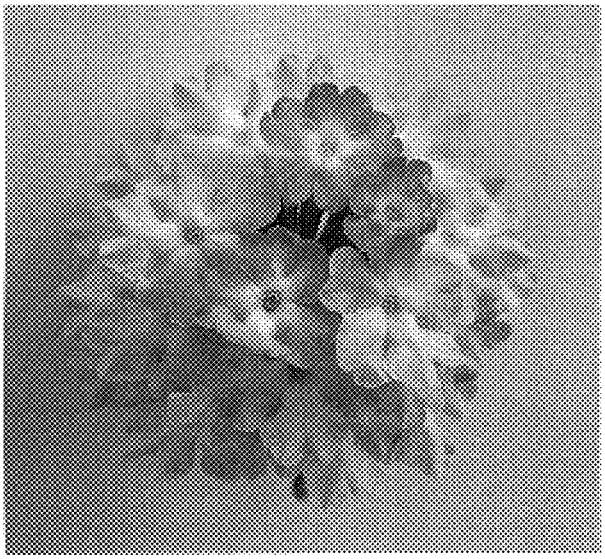
FIG. 2 illustrates a close-up view of an individual inflorescence of 'Balazlipi'.
Figure 3:
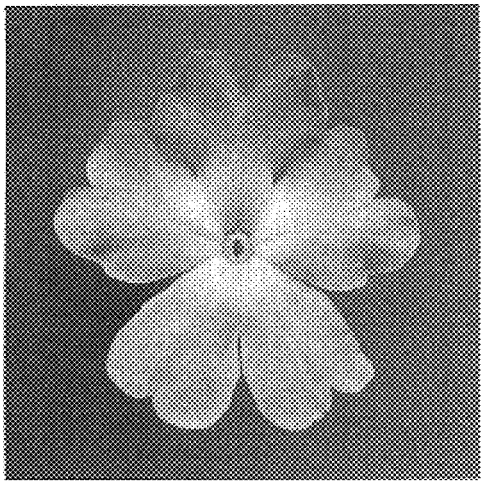
FIG. 3 illustrates a close-up view of an individual flower of 'Balazlipi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Mar. 1, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 13 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Verbena×hybrida* cultivar Balazlipi.

Parentage:

*Female parent.*—Aztec® Dark Purple Improved 'Balazdapi', U.S. Plant Pat. No. 12,807.

*Male parent.*—Proprietary *Verbena×hybrida* breeding selection designated 1671-1, not patented.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fibrous.

*Rooting habit.*—Freely branching.

Plant description:

*Commercial crop time.*—Approximately 5 to 7 weeks from a rooted cutting.

*Growth habit and general appearance.*—Moderately vigorous and trailing, spreading.

*Size.*—Height from soil level to top of plant plane: Approximately 12.3 cm. Width: Approximately 38.0 cm.

*Branching habit.*—Freely branching. Quantity of main branches per plant. Approximately 4.

*Branch.*—Shape: Square in cross section. Strength: Strong. Length: Approximately 25.5 cm. Diameter: Approximately 3.0 mm. Length of central internode: Approximately 1.7 cm. Texture: Densely pubescent. Color of young and mature stems: 144A.

Foliage description:

*Generation description.*—Quantity of leaves per main branch: Approximately 23. Fragrance: None. Form: Simple. Arrangement: Opposite.

*Leaves.*—Aspect: Perpendicular to stem. Shape: Ovate. Margin: Serrate. Apex: Acute. Base: Truncate. Venation pattern: Pinnate. Length of mature leaf: Approximately 4.2 cm. Width of mature leaf: Approximately 2.7 cm. Texture of upper surface: Densely pubescent. Texture of lower surface: sparsely pubescent and densely glandular pubescent on veins. Color of upper surface of young and mature foliage: 137A with venation of 144D. Color of lower surface of young and mature foliage: 138B with venation of 145C.

*Petiole.*—Length: Approximately 5.2 mm. Diameter: Approximately 2.0 mm. Texture: Densely pubescent. Color: 144D.

Flowering description:

*Flowering habit.*—'Balazlipi' is freely flowering under outdoor growing conditions with substantially continuous blooming from spring through autumn and year round in greenhouse environment.

*Lastingness of individual flower on the plant.*—Approximately 5 to 7 days.

Inflorescence description:

*General description.*—Type: Corymb. Quantity per plant: Approximately 5. Fragrance: None. Length or height: Approximately 3.4 cm. Width: Approximately 6.0 cm. Quantity of fully open flowers per inflorescence: Approximately 25.

*Peduncle.*—Strength: Strong. Aspect: Erect. Length: Approximately 3.9 cm. Diameter: Approximately 2.0 mm. Texture: Densely pubescent with a mixture of glandular and nonglandular hairs. Color: 144A.

Flower description:

*General description.*—Type: Sessile, salverform.

*Bud.*—Rate of opening: Generally takes 2 to 3 days for bud to progress from first color to fully open flower.

*Bud just before opening.*—Shape: Elongated, globular at apex. Length: Approximately 1.4 cm. Diameter: Approximately 3.3 mm. Color: 62D.

*Corolla.*—Shape: Round. Diameter: Approximately 2.2 cm. Depth: Approximately 2.5 cm.

*Petals.*—Quantity: 5, fused at base forming a tube. Shape: Obovate. Appearance: Velvety. Margin: Entire. Apex: Emarginate. Length of upper petal from tube: Approximately 1.1 cm. Width of upper petal: Approximately 1.1 cm. Length of lateral petals from tube: Approximately 1.0 cm. Width of lateral petals: Approximately 9.2 mm. Length of lower petals from tube: Approximately 1.0 cm. Width of lower petals: Approximately 8.0 mm. Texture of upper surface: Glabrous. Texture of lower surface: Sparsely glandular pubescent. Color of upper surface when first open: 62A transitioning to N155B at base. Color of lower surface when first open: 62C transitioning to N155B at base. Color of upper surface when fully open: 62C transitioning to N155B at base. Color of lower surface when fully open: 62D transitioning to N155B at base. Whisker color surrounding the opening of the corolla tube: 155D.

*Corolla tube.*—Length: Approximately 2.0 cm. Diameter at distal end: Approximately 2.2 mm. Diameter at proximal end: Approximately 1.3 mm. Texture of inner surface: Densely pubescent. Texture of outer surface: Sparsely glandular pubescent. Color of inner surface: 145D at proximal end transitioning to 145B at distal end. Color of outer surface: 145D.

*Calyx.*—Shape: Tubular with 5 acute tips. Length: Approximately 1.2 cm. Width: Approximately 2.0 mm.

*Sepals.*—Quantity per flower: 5, fused at base. Shape: Linear. Apex: Acute. Length: Approximately 1.2 cm. Width: Approximately 1.0 mm. Texture: Densely pubescent with a mixture of glandular and nonglandular hairs. Gland color: Colorless. Color of upper and lower surfaces: 137A, transparent where margins fuse. Stipule shape: Lanceolate. Stipule apex: Acuminate. Stipule length: Approximately 6.9 mm. Stipule width at base: Approximately 1.6 mm. Stipule texture: Densely pubescent with a mixture of glandular and nonglandular hairs. Stipule gland color: Colorless. Stipule color: 144A at base transitioning to 137A at apex.

*Reproductive organs.*—Androecium: Stamen quantity: 4 per flower. Stamen length: Approximately 1.8 mm. Anther shape: Ovoid. Anther length: Approximately 1.0 mm. Anther color: 150C. Pollen amount: Sparse. Pollen color: 150D. Gynoecium: Pistil quantity: 1 per flower. Pistil length: Approximately 1.8 cm. Stigma shape: Biparted. Stigma length: Less than 1 mm. Stigma color: 143A. Style length: Approximately 1.7 cm. Style color: 144D. Ovary diameter: Approximately 1.0 mm. Ovary texture: Glabrous. Ovary color: 144A.

Seed and fruit production: Neither seed not fruit production has been observed.

Disease and pest resistance: Resistance to pathogens and pests common to *Verbena* has not been observed.

What is claimed is:

1. A new and distinct cultivar of *Verbena* plant named 'Balazlipi', substantially as herein shown and described.

* * * * *